United States Patent
Wilkinson

(10) Patent No.: US 10,524,710 B2
(45) Date of Patent: Jan. 7, 2020

(54) PASSIVE DOUBLE DRIVE MEMBER ACTIVATED SAFETY BLOOD COLLECTION DEVICE

(71) Applicant: Becton, Dickinson and Company, Franklin Lakes, NJ (US)

(72) Inventor: Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 155 days.

(21) Appl. No.: 13/677,662

(22) Filed: Nov. 15, 2012

(65) Prior Publication Data

US 2014/0135652 A1   May 15, 2014

(51) Int. Cl.
*A61B 5/153* (2006.01)

(52) U.S. Cl.
CPC .................................. *A61B 5/153* (2013.01)

(58) Field of Classification Search
CPC ............................. A61B 5/15; A61B 5/150633
See application file for complete search history.

(56) References Cited

U.S. PATENT DOCUMENTS

| | | |
|---|---|---|
| 3,640,275 A | 2/1972 | Burke et al. |
| 3,840,008 A | 10/1974 | Noiles |
| 4,139,009 A | 2/1979 | Alvarez |
| 4,725,267 A | 2/1988 | Vaillancourt |
| 4,735,618 A | 4/1988 | Hagen |
| 4,790,828 A | 12/1988 | Dombrowski et al. |
| 4,867,172 A | 9/1989 | Haber et al. |
| 4,867,746 A | 9/1989 | Dufresne |
| 4,892,521 A | 1/1990 | Laico et al. |
| 4,909,794 A | 3/1990 | Haber et al. |
| 4,911,694 A | 3/1990 | Dolan |
| 4,955,866 A | 9/1990 | Corey |

(Continued)

FOREIGN PATENT DOCUMENTS

| | | |
|---|---|---|
| CN | 1449846 A | 10/2003 |
| CN | 1449847 A | 10/2003 |

(Continued)

OTHER PUBLICATIONS

CN 1449846, 2003/0181871.
CN 1449847, 2003/0181870.
CN 1636607, U.S. Pat. No. 6,832,992.

*Primary Examiner* — Daniel L Cerioni
*Assistant Examiner* — Yasmeen S Warsi
(74) *Attorney, Agent, or Firm* — The Webb Law Firm

(57) ABSTRACT

A shieldable needle device including a drive member is disclosed. The drive member is extendable between a biased position and an extended position for moving a tip guard from an first position to a second position in which the tip guard shields a distal end of the needle cannula. The shieldable needle device includes a pair of wings extending laterally from opposing sides of the hub that are movable between a laterally extending position and a dorsal position. With the wings in the dorsal position, the wings retain the drive member in the biased position thereby maintaining the tip guard in the first position. Movement of the wings from the dorsal position to the laterally extending position releases retainment of the drive member. A second drive member may be included.

11 Claims, 11 Drawing Sheets

(56) References Cited

U.S. PATENT DOCUMENTS

| | | |
|---|---|---|
| 4,998,922 A | 3/1991 | Kuracina et al. |
| 5,059,180 A | 10/1991 | McLees |
| 5,098,401 A | 3/1992 | De Lange |
| 5,176,655 A | 1/1993 | McCormick et al. |
| 5,242,418 A | 9/1993 | Weinstein |
| 5,250,031 A | 10/1993 | Kaplan et al. |
| 5,256,152 A | 10/1993 | Marks |
| 5,271,070 A | 12/1993 | Truong et al. |
| 5,295,972 A | 3/1994 | Mischenko |
| 5,328,483 A | 7/1994 | Jacoby |
| 5,334,155 A | 8/1994 | Sobel |
| 5,348,544 A | 9/1994 | Sweeney et al. |
| 5,423,766 A | 6/1995 | Di Desare |
| 5,538,508 A | 7/1996 | Steyn |
| 5,549,571 A | 8/1996 | Sak |
| 5,562,633 A | 10/1996 | Wozencroft |
| 5,584,818 A | 12/1996 | Morrison |
| 5,630,803 A | 5/1997 | Tamaro |
| 5,688,241 A | 11/1997 | Asbaghi |
| 5,713,872 A | 2/1998 | Feuerborn et al. |
| 5,716,872 A | 2/1998 | Isobe |
| 5,735,827 A | 4/1998 | Adwers et al. |
| 5,738,665 A | 4/1998 | Caizza et al. |
| 5,755,699 A | 5/1998 | Blecher et al. |
| 5,779,679 A | 7/1998 | Shaw |
| 5,833,670 A | 11/1998 | Dillon et al. |
| 5,951,525 A | 9/1999 | Thorne et al. |
| 6,210,371 B1 | 4/2001 | Shaw |
| 6,224,576 B1 | 5/2001 | Thorne et al. |
| 6,254,577 B1 | 7/2001 | Huet |
| 6,261,264 B1 | 7/2001 | Tamaro |
| D452,003 S | 12/2001 | Niermann |
| D452,313 S | 12/2001 | Niermann |
| D452,314 S | 12/2001 | Niermann |
| 6,375,640 B1 | 4/2002 | Teraoka |
| 6,409,706 B1 | 6/2002 | Loy |
| 6,537,259 B1 | 3/2003 | Niermann |
| 6,682,510 B2 | 1/2004 | Niermann |
| 6,832,992 B2 | 12/2004 | Wilkinson |
| 6,918,891 B2 | 7/2005 | Bressler et al. |
| 2002/0099339 A1* | 7/2002 | Niermann ........... A61M 5/3275 604/263 |
| 2002/0111566 A1 | 8/2002 | Maclean Crawford et al. |
| 2003/0036731 A1 | 2/2003 | Wilkinson et al. |
| 2003/0135157 A1* | 7/2003 | Saulenas ............ A61M 5/3213 604/110 |
| 2003/0181870 A1* | 9/2003 | Bressler ............ A61M 25/0637 604/263 |
| 2003/0181871 A1 | 9/2003 | Wilkinson et al. |
| 2004/0111057 A1 | 6/2004 | Wilkinson |
| 2005/0137528 A1 | 6/2005 | Wilkinson |
| 2011/0306989 A1* | 12/2011 | Darois et al. ................. 606/144 |

FOREIGN PATENT DOCUMENTS

| | | |
|---|---|---|
| CN | 1636607 A | 7/2005 |
| EP | 0713710 A1 | 5/1996 |
| EP | 1132103 A1 | 9/2001 |
| EP | 1221303 A2 | 7/2002 |
| EP | 1254677 A1 | 11/2002 |
| EP | 1346738 A1 | 9/2003 |
| EP | 1369142 A1 | 12/2003 |
| EP | 1374772 A1 | 1/2004 |
| EP | 1430834 A2 | 6/2004 |
| EP | 1457228 A2 | 9/2004 |
| EP | 1543859 A1 | 6/2005 |
| EP | 1449554 B1 | 4/2009 |
| GB | 2301036 A | 11/1996 |
| JP | 2004249100 A | 9/2004 |
| WO | 9419036 A1 | 9/1994 |
| WO | 03026731 A1 | 4/2003 |

* cited by examiner

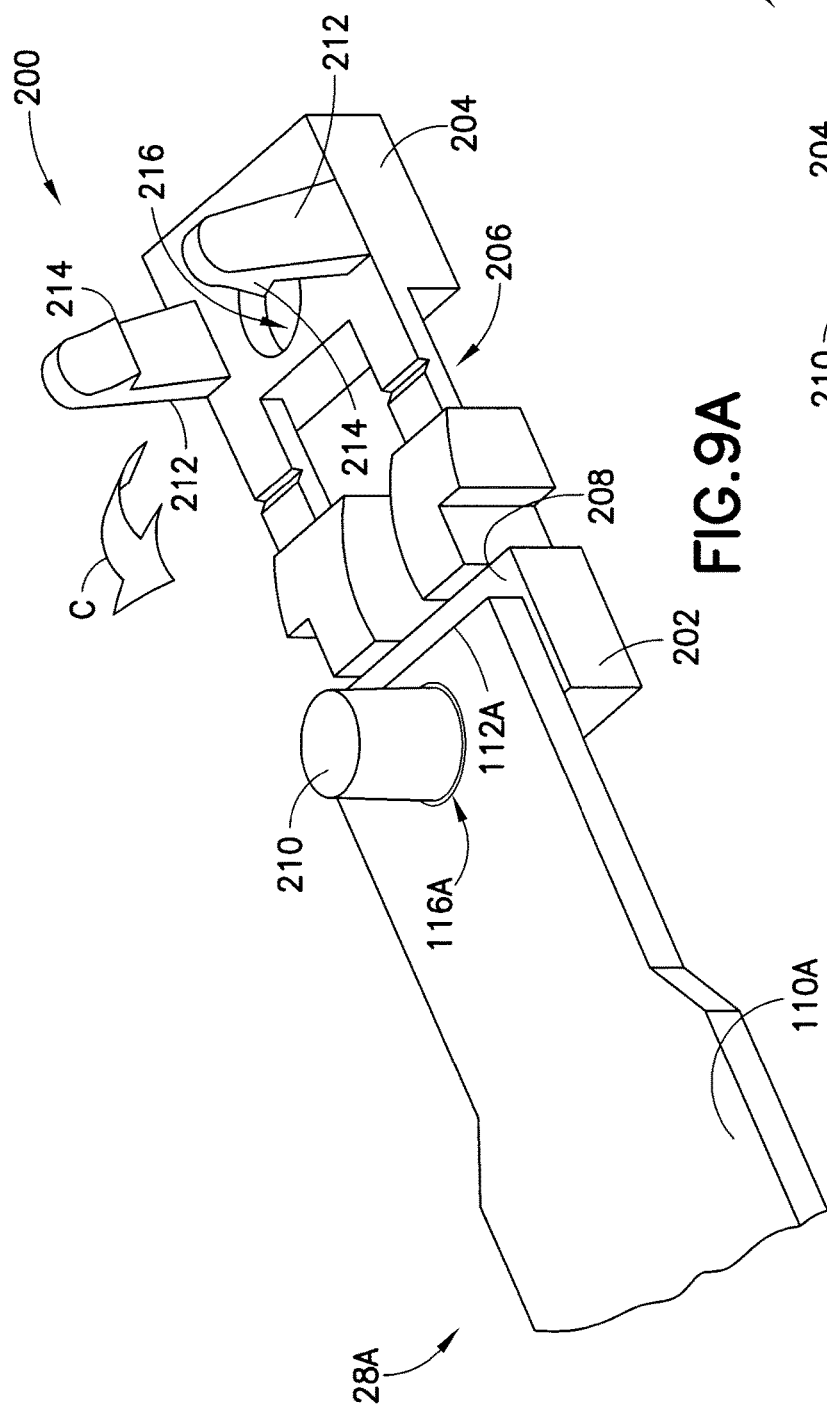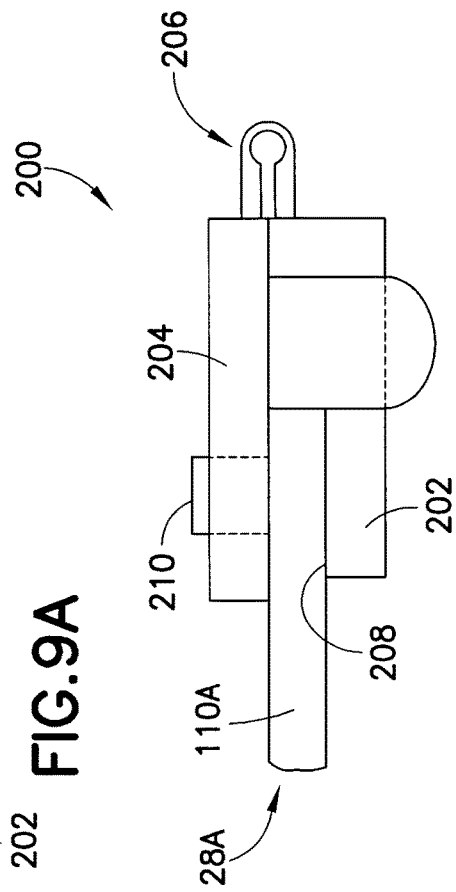

PASSIVE DOUBLE DRIVE MEMBER ACTIVATED SAFETY BLOOD COLLECTION DEVICE

BACKGROUND OF THE INVENTION

1. Field of the Disclosure

The present disclosure relates generally to a blood collection device for safe and convenient handling of needles. More particularly, the present disclosure relates to an inexpensive disposable blood collection device including a passively activated safety shield device for protectively shielding a pointed end of a needle assembly.

2. Description of the Related Art

Disposable medical devices that have piercing elements are typically used for administering a medication or withdrawing a fluid, such as blood collecting needles or fluid handling needles. Current medical practice requires that the fluid containers and needle assemblies used in such systems be inexpensive and readily disposable. Consequently, existing blood collection systems, for example, typically employ some form of a durable, reusable holder on which detachable and disposable needles and fluid collection tubes may be mounted. A blood collection system of this nature can be assembled prior to use and then disassembled after usage. Accordingly, these blood collection systems allow repeated use of the relatively expensive holder upon replacement of the relatively inexpensive needle and/or fluid collection tube. In addition to reducing the cost of collecting blood specimens, these blood collection systems also help minimize the production of hazardous medical waste.

A blood collection set or intravenous (IV) infusion set typically includes a needle cannula having a proximal end, a pointed distal end, and a lumen extending therebetween. The proximal end of the needle cannula is securely mounted in a plastic hub with a central passage that communicates with the lumen through the needle cannula. A thin flexible thermoplastic tube is connected to the hub and communicates with the lumen of the needle cannula. The end of the plastic tube, remote from the needle cannula, may include a fixture for connecting the needle cannula to a blood collection tube or some other receptacle. The specific construction of the fixture will depend upon the characteristics of the receptacle to which the fixture will be connected.

In order to reduce the risk of incurring an accidental needle-stick wound, protection of used needle tips becomes important. With concern about infection and transmission of diseases, methods and devices to enclose the used disposable needle have become very important and in great demand. For example, needle assemblies commonly employ a safety shield that can be moved into shielding engagement with a used needle cannula without risking an accidental needle stick.

SUMMARY OF THE INVENTION

The present disclosure provides a shieldable needle device including in one embodiment, a first drive member and a second drive member. The first drive member and the second drive member are each extendable between a folded biased position and an extended position for moving a tip guard from a proximal position adjacent a hub supporting the proximal end of a needle cannula to a distal position in which the tip guard protectively surrounds the distal end of the needle cannula. The shieldable needle device includes a wing assembly having a pair of wings extending laterally from opposing sides of the hub and that are movable between a laterally extending position and a dorsal position. With the pair of wings in the dorsal position, the wings retain the first drive member and the second drive member in the folded biased position thereby maintaining the tip guard in the proximal position. Movement of the wings from the dorsal position to the laterally extending position releases retainment of the first drive member and the second drive member thereby allowing the first drive member and the second drive member to unfold to the extended position and move the tip guard from the proximal position to the distal position.

In all embodiments of the shieldable needle device of the present disclosure, the first drive member is separate and distinct from the second drive member. Advantageously, by having two separate drive members, the shieldable needle device of the present disclosure provides for better and more consistent locking out of the tip guard to the distal position in which the tip guard protectively surrounds and shields the distal end of the needle cannula. This is achieved because by having two separate drive members, a greater force that the two drive members extend from the folded biased position to the extended position can be achieved. In this manner, the shieldable needle device of the present disclosure provides more consistent locking out of the tip guard to the distal position in which the tip guard protectively surrounds and shields the distal end of the needle cannula. Furthermore, by having two separate drive members, more control can be exerted over the above described extension force of the two drive members to the extended position.

Another advantage of the two drive members of the shieldable needle device of the present disclosure is that the two drive members provide a greater shielding of the needle cannula. For example, referring to FIGS. 6 and 7, by having two separate drive members, a greater area of the needle cannula is protectively surrounded and safely shielded. As shown in FIGS. 6 and 7, the two drive members, together with the tip guard assembly, substantially completely surround and shield the needle cannula. Furthermore, the two separate drive members provide additional side shielding guards for the needle cannula. In this manner, no portion of the needle cannula is exposed thereby significantly reducing the risk of accidental needle stick injuries.

In accordance with an embodiment of the present invention, a shieldable needle device includes a needle cannula having a proximal end and a distal end, and a hub supporting at least a portion of the needle cannula. The device further includes a wing assembly having at least a pair of wings extending from opposing sides of the hub, the pair of wings movable between a laterally extending position and a dorsal position. The device also includes a tip guard axially movable with respect to the needle cannula from a first position adjacent the hub to a second position in which the tip guard shields the distal end of the needle cannula. A drive member is also provided which is extendable between a biased position and an extended position for moving the tip guard from the first position to the second position, the drive member having a proximal end engaged with the hub and a distal end engaged with the tip guard. With the pair of wings in the dorsal position, the pair of wings retain the drive member in the biased position thereby maintaining the tip guard in the proximal position, and movement of the pair of wings from the dorsal position to the laterally extending position releases the drive member thereby allowing the drive member to transition to the extended position and advance the tip guard from the proximal position to the distal position.

In certain configurations, the device includes a second drive member extendable between a biased position and an extended position for moving the tip guard from the first position to the second position, the second drive member having a proximal end engaged with the hub and a distal end engaged with the tip guard. In certain configurations, with the pair of wings in the dorsal position, the pair of wings retain the drive member and the second drive member in the biased position thereby maintaining the tip guard in the proximal position. Movement of the pair of wings from the dorsal position to the laterally extending position releases the drive member and the second drive member, thereby allowing the drive member and the second drive member to transition to the extended position and advance the tip guard from the proximal position to the distal position. The proximal end of the drive member may be connected to an opposite side of the hub from the proximal end of the second drive member. The distal end of the drive member may be connected to an opposite side of the tip guard from the distal end of the second drive member.

In other configurations, the device may further include a cover protectively surrounding the needle cannula and maintaining the pair of wings in the dorsal position. The cover may define a slot area for receiving and maintaining the pair of wings in the dorsal position. In certain configurations, the pair of wings are formed with the hub. The pair of wings may be formed of a resilient flexible material. Optionally, the drive member is formed of a resilient flexible material.

The tip guard may include a tip guard housing formed from a plastic material and a metallic spring clip mounted to the tip guard housing. The spring clip may be biased against the needle cannula with the tip guard in the proximal position and the spring clip may be disposed over the distal end of the needle cannula with the tip guard in the distal position. The drive member may be at least partially folded in the biased position. In certain situations, both the drive member and the second drive member are at least partially folded in the biased position.

In accordance with another embodiment of the present invention, a shieldable needle device includes a needle cannula having a proximal end and a distal end, and a hub supporting at least a portion of the needle cannula. The device includes a wing assembly having at least a pair of wings extending from opposing sides of the hub, the pair of wings movable between a laterally extending position and a dorsal position, with the pair of wings in the dorsal position a gap is formed between the hub and the pair of wings. The device also includes a tip guard axially movable with respect to the needle cannula from a first position adjacent the hub to a second position in which the tip guard shields the distal end of the needle cannula. The device further includes a drive member extendable between a biased position and an extended position for moving the tip guard from the first position to the second position, the drive member having a proximal end engaged with the hub and a distal end engaged with the tip guard. With the pair of wings in the dorsal position and the drive member in the biased position, a portion of the drive member is retained within the gap between the hub and the pair of wings.

In certain configurations, the device further includes a second drive member extendable between a biased position and an extended position for moving the tip guard from the first position to the second position, the second drive member having a proximal end engaged with the hub and a distal end engaged with the tip guard. With the pair of wings in the dorsal position and the drive member and the second drive member in the biased position, a portion of at least one of the drive member and the second drive member may be retained within the gap between the hub and the pair of wings. With the pair of wings in the dorsal position and the drive member and the second drive member in the biased position, a portion of both the drive member and the second drive member may be retained within the gap between the hub and the pair of wings. The pair of wings may retain the drive member and the second drive member in a folded position thereby maintaining the tip guard in the proximal position, and movement of the pair of wings from the dorsal position to the laterally extending position may release retainment of the drive member and the second drive member thereby allowing the drive member and the second drive member to unfold to the extended position and move the tip guard from the proximal position to the distal position.

In certain configurations, the drive member is separate from the second drive member. The proximal end of the drive member may be connected to an opposite side of the hub from the proximal end of the second drive member. The distal end of the drive member may be connected to an opposite side of the tip guard from the distal end of the second drive member. The drive member may be formed of a resilient flexible material.

Optionally, the tip guard includes a tip guard housing formed from a plastic material and a metallic spring clip mounted to the tip guard housing. The spring clip may be biased against the needle cannula with the tip guard in the proximal position and the spring clip may be disposed over the distal end of the needle cannula with the tip guard in the distal position.

In accordance with another embodiment of the present invention, a shieldable needle device includes a needle cannula having a proximal end and a distal end, and a retainer member supporting the proximal end of the needle cannula, the retainer member movable between an open position and a retaining position. The device also includes a tip guard axially movable with respect to the needle cannula from a first position adjacent the retainer member to a second position in which the tip guard shields the distal end of the needle cannula. The device includes a first drive member extendable between a biased position and an extended position for moving the tip guard from the first position to the second position, the first drive member having a proximal end connected to the retainer member and a distal end connected to the tip guard. The device also includes a second drive member extendable between a biased position and an extended position for moving the tip guard from the first position to the second position, the second drive member having a proximal end connected to the retainer member and a distal end connected to the tip guard. With the retainer member in the retaining position, the retainer member retains the first drive member and the second drive member in the biased position thereby maintaining the tip guard in the first position. Movement of the retainer member from the retaining position to the open position releases retainment of the first drive member and the second drive member thereby allowing the first drive member and the second drive member to transition to the extended position and move the tip guard from the first position to the second position.

In certain configurations, the first drive member and the second drive member are at least partially folded in the biased position. Optionally, movement of the retainer member from the retaining position to the open position releases retainment of the first drive member and the second drive member thereby allowing the first drive member and the second drive member to unfold to the extended position and move the tip guard from the first position to the second position.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings.

FIG. 9A is a perspective view of an exemplary connection means, in an open position, between a first drive member or a second drive member and a hub or a tip guard assembly of the shieldable needle device of FIG. 1 in accordance with an embodiment of the present invention.

FIG. 9B is a side elevation on cross-sectional view of the exemplary connection on means of FIG. 9A, in a locked position, between a first drive member or a second drive member and a hub or a tip guard assembly of the shieldable needle device of FIG. 1 in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
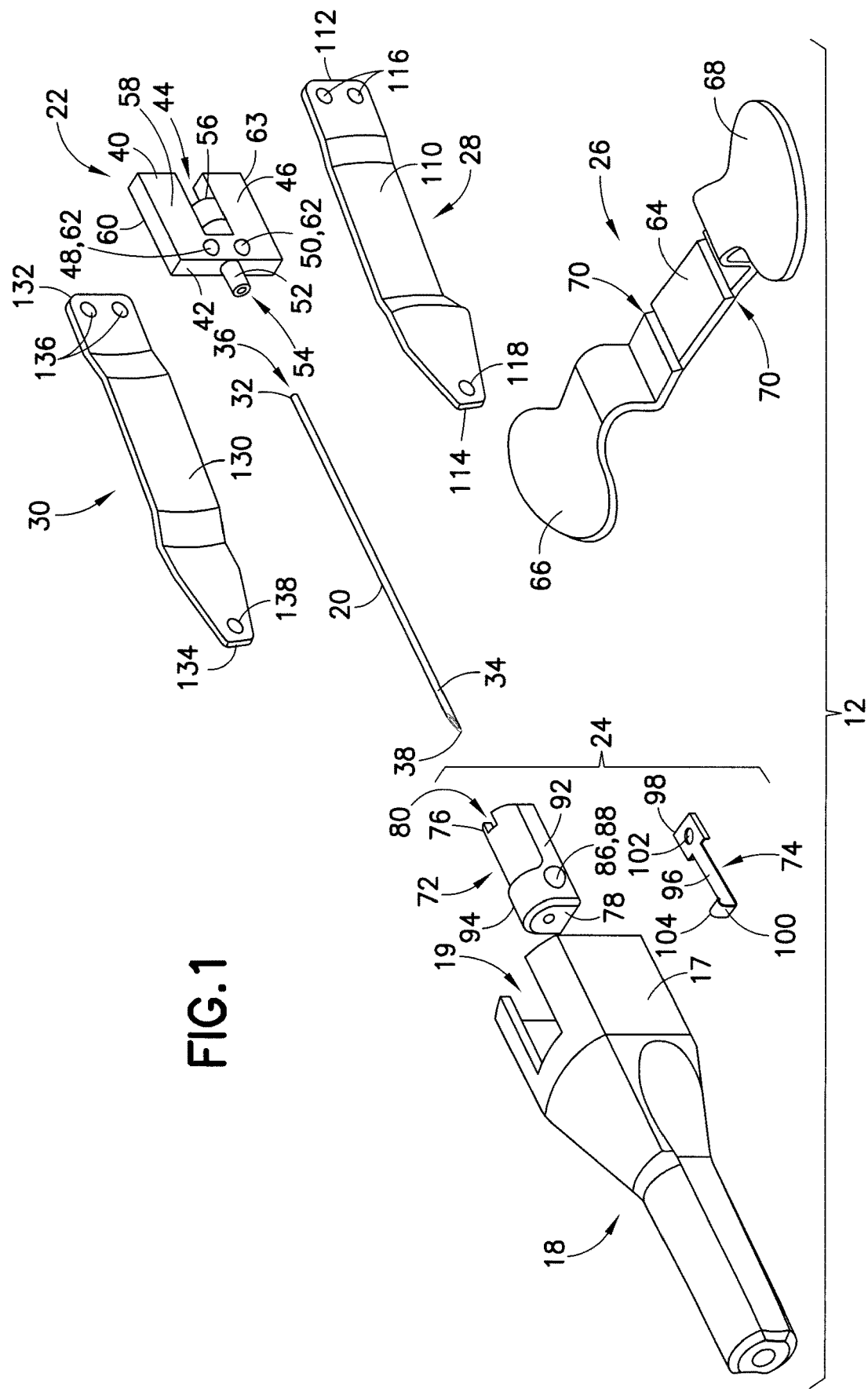
FIG. 1 is an exploded, perspective view of a shieldable needle device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a needle assembly adapted for contact with a patient, and "proximal" refers to the opposite direction of distal, i.e., away from the end of a needle assembly adapted for contact with a patient. For purposes of this disclosure, the above-mentioned references are used in the description of the components of a shieldable needle device in accordance with the present disclosure.

Figure 2:
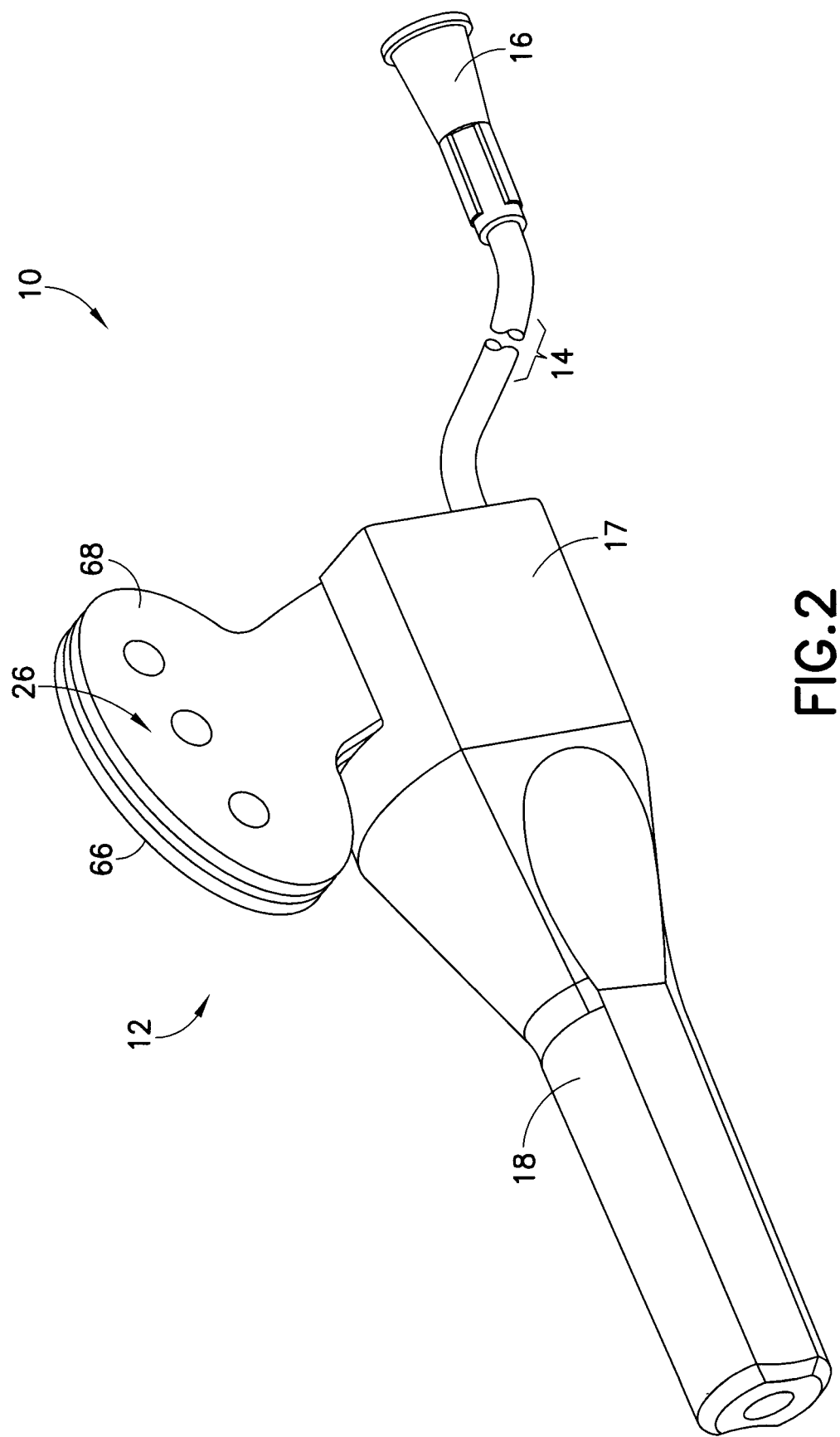
FIG. 2 is an assembled, perspective view of the shieldable needle device of FIG. 1 in accordance with an embodiment of the present invention.

Referring to FIGS. 1 and 2, a blood collection assembly 10 includes a shieldable needle device 12, a flexible tube 14 extending from shieldable needle device 12, a fixture 16 mounted to tube 14, and a packaging cover 18 removably mounted to portions of shieldable needle device 12 opposite tube 14. In one embodiment, cover 18 may be removably mounted to shieldable needle device 12 through a frictional engagement, interference fit, or similar securement method. Blood collection assembly 10 includes a needle cannula 20 having a proximal end 32, an opposing distal end 34, and a lumen 36 extending between the ends. Proximal end 32 of needle cannula 20 is securely mounted with a hub 22 so that a central passage 44 of hub 22 is in fluid communication with lumen 36 of needle cannula 20.

Thin flexible thermoplastic tubing 14 may be connected to hub 22 so that tubing 14 is in fluid communication with lumen 36 of needle cannula 20. For example, flexible tubing 14 can be mounted to a proximal end 40 of hub 22 such that the passage through tubing 14 communicates with lumen 36 of needle cannula 20. The end of tubing 14 remote from needle cannula 20 may include fixture 16 mounted thereon for connecting needle cannula 20 to a blood collection tube or some other receptacle. For example, fixture 16 enables needle cannula 20 and tubing 14 to be placed in communication with an appropriate receptacle, such as a blood collection tube. The specific construction of fixture 16 will depend upon the characteristics of the receptacle to which fixture 16 will be connected.

Blood collection assembly 10 can be packaged substantially in the condition shown in FIG. 2 in protective packaging, such as in a blister package. Prior to use, blood collection assembly 10 is removed from any protective package, and fixture 16 may be connected to an appropriate receptacle for providing fluid communication with lumen 36 extending through needle cannula 20 as will described in more detail below.

Referring to FIGS. 1 and 4-8, shieldable needle device 12 includes packaging cover 18, needle cannula 20, hub 22, a tip guard assembly 24, a wing assembly 26, a first drive member 28, and a second drive member 30. First drive member 28 and second drive member 30 are configured for moving tip guard assembly 24 as will be described in more detail below.

Figure 5:
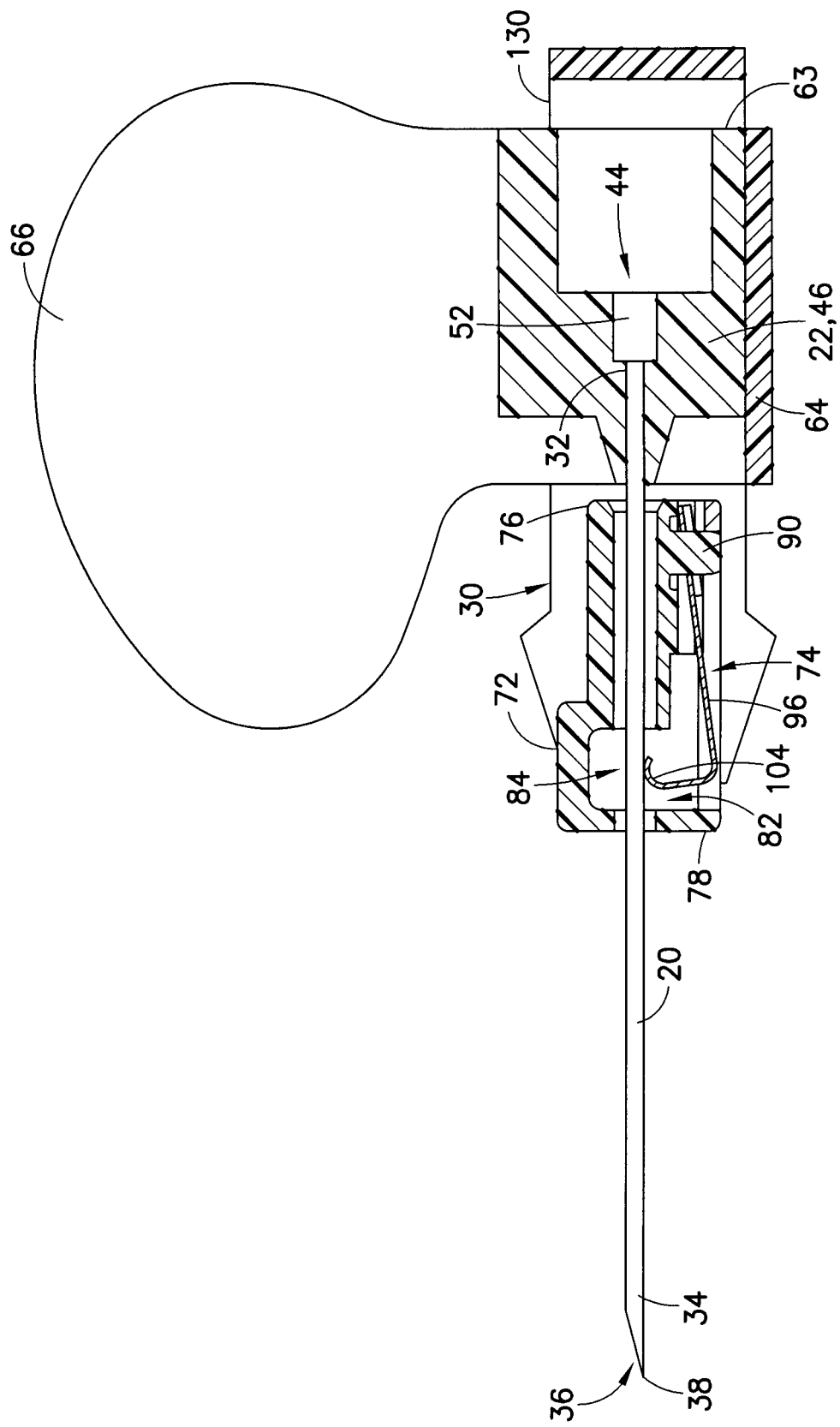
FIG. 5 is a cross-sectional view taken along line 5-5 of the shieldable needle device of FIG. 4 in accordance with an embodiment of the present invention.
Figure 6:
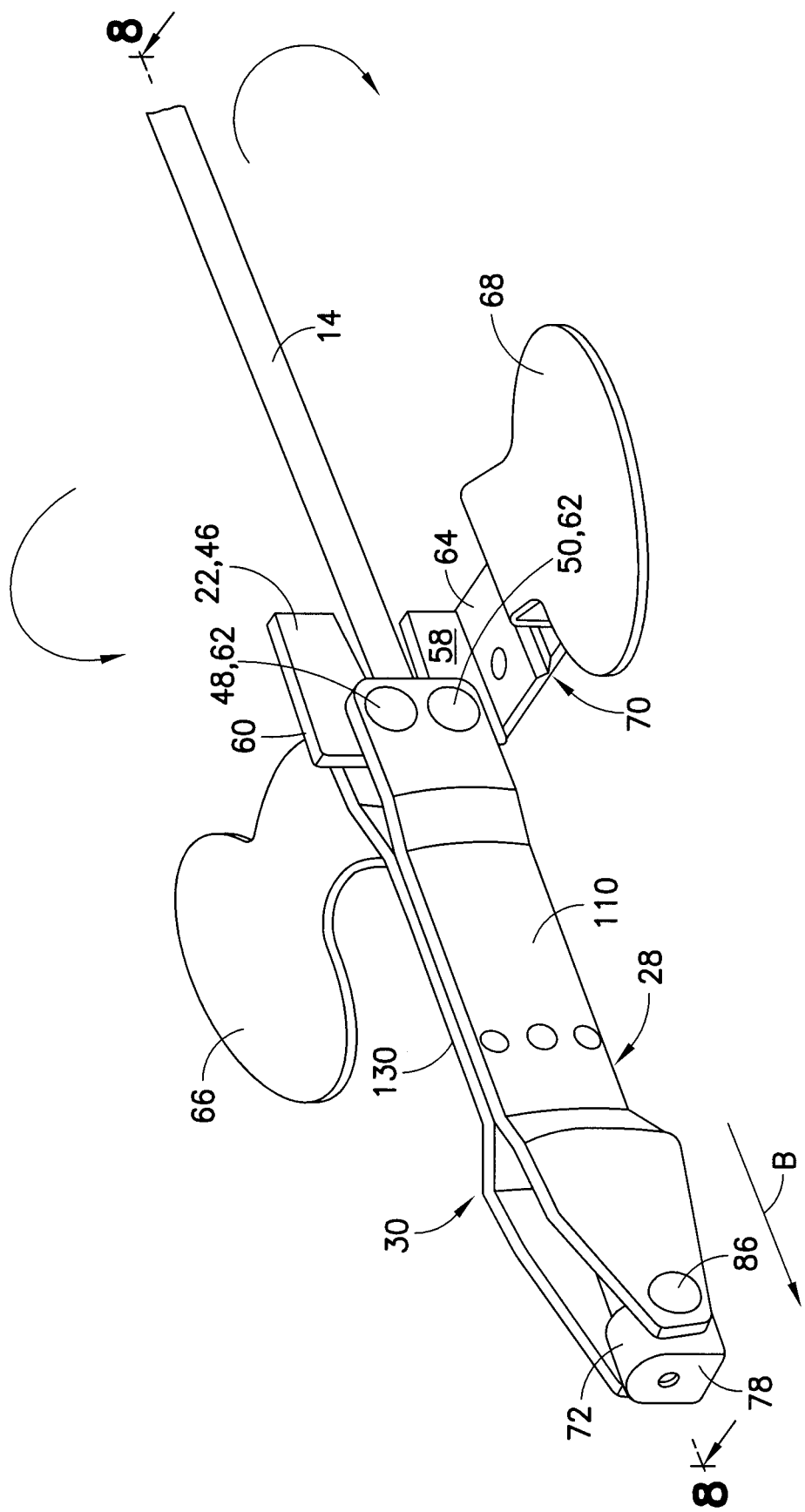
FIG. 6 is a perspective view of the shieldable needle device of FIG. 2 with the packaging cover removed, with the wing assembly in a laterally extending position, and the first and second drive members in an extended position in accordance with an embodiment of the present invention.
Figure 7:
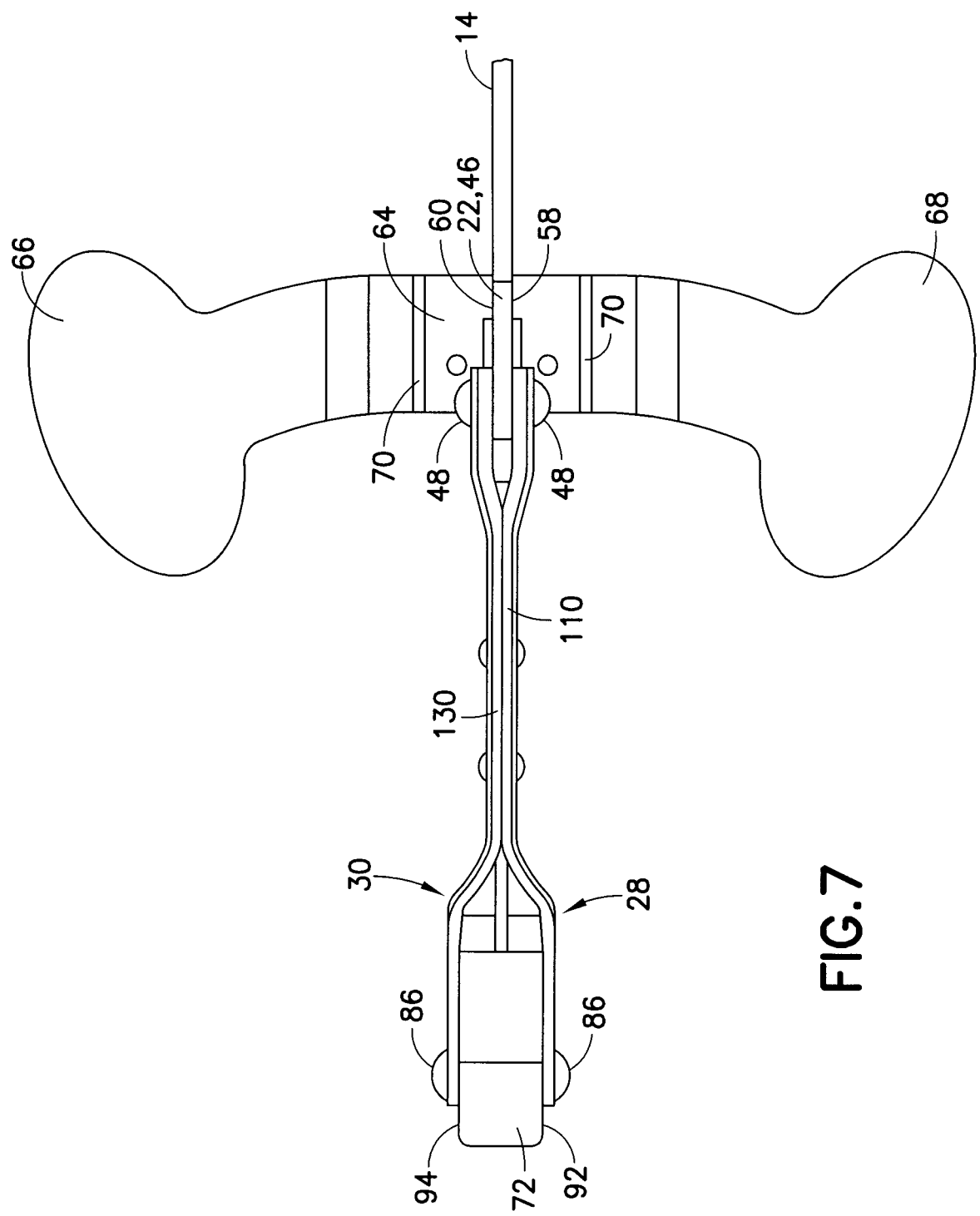
FIG. 7 is a plan view of the shieldable needle device of FIG. 6 in accordance with an embodiment of the present invention.

Referring to FIG. 1, first drive member 28 is separate and distinct from second drive member 30. By having two separate drive members 28 and 30, shieldable needle device 12 provides for better and more consistent locking out of tip guard assembly 24 to the distal position (FIGS. 6-8) in which tip guard assembly 24 protectively surrounds and shields distal end 34 of needle cannula 20. This is achieved because by having two separate drive members 28 and 30, a greater force that drive members 28 and 30 extend from the folded biased position (FIGS. 2-5) to the extended position (FIGS. 6-8) can be achieved. In this manner, shieldable needle device 12 provides more consistent locking out of tip guard assembly 24 to the distal position in which the tip guard assembly 24 protectively surrounds and shields distal end 34 of needle cannula 20. The two drive members 28 and 30 also provide a greater shielding of needle cannula 20. Referring to FIGS. 6 and 7, by having two separate drive members 28 and 30, a greater area of needle cannula 20 is protectively surrounded and safely shielded. As shown in FIGS. 6 and 7, the two drive members 28 and 30, together with tip guard assembly 24, substantially completely surround and shield needle cannula 20. Furthermore, the two separate drive members 28 and 30 provide additional side shielding guards for needle cannula 20. In this manner, no portion of needle cannula 20 is exposed thereby significantly reducing the risk of accidental needle stick injuries.

Referring to FIG. 1, needle cannula 20 includes a proximal end 32 and an opposing distal end 34, with lumen 36 extending through needle cannula 20 from proximal end 32 to distal end 34. Distal end 34 of needle cannula 20 is beveled to define a sharp puncture tip 38, such as an intravenous puncture tip. Puncture tip 38 is provided for insertion into a patient's blood vessel, such as a vein, and is therefore designed to provide ease of insertion and minimal discomfort during venipuncture.

Referring to FIG. 1, shieldable needle device 12 includes hub 22. In one embodiment, hub 22 is a unitary structure, desirably molded from a thermoplastic material. In another embodiment, hub 22 may be integrally formed with wing assembly 26 as discussed below. In such an embodiment, the integral component of hub 22 and wing assembly 26 forms a retainer member that supports proximal end 32 of needle cannula 20 and that is movable between an open position (FIGS. 6-8) and a retaining position (FIGS. 2-5).

Hub 22 includes a proximal end 40, an opposing distal end 42, and is defined by a rigid structure or hub structure 46 extending between the ends. Hub 22 also includes hub connecting tube 52 disposed within a central cavity portion of hub structure 46 and defining a distal opening 54 for receiving proximal end 32 of needle cannula 20. In this manner, hub 22 is configured to support proximal end 32 of needle cannula 20. Needle cannula 20 can be positioned within distal opening 54 of hub 22 so that a portion of needle cannula 20 extends from distal end 42 of hub 22. In one embodiment, needle cannula 20 and hub 22 may be separate parts which are fixedly attached and secured through an appropriate medical grade adhesive, for example, epoxy or similar adhesive material. In another embodiment, needle cannula 20 and hub 22 may form an integral component. For example, needle cannula 20 and hub 22 may be integrally molded in a two-step molding process. Hub connecting tube 52 also defines a proximal opening 56 which is adapted to receive flexible tube 14 as shown in FIG. 2, or other medical device, such as a tube holder or similar component. Hub connecting tube 52 also defines a central passage 44 extending through hub connecting tube 52 from proximal end 40 to distal end 42.

Hub 22 includes structure for mating with first drive member 28 and second drive member 30. For example, a first side surface 58 of distal end 42 of hub 22 may include a first connection element 48 and a second connection element 50 for connection with first drive member 28. An opposing second side surface 60 of distal end 42 of hub 22 may also include a first connection element 48 and a second connection element 50 for connection with second drive member 30. In one embodiment, first connection element 48 and second connection element 50 may include two button elements 62 for connection with first drive member 28 and second drive member 30, respectively, as will be discussed in more detail below. In other embodiments, hub 22 may include different types of structures for mating with first drive member 28 and second drive member 30 as will be described in more detail below and with reference to FIGS. 9A-11.

Referring to FIG. 1, shieldable needle device 12 includes wing assembly 26. In one embodiment, wing assembly 26 may be a unitary structure, desirably formed of a flexible material. As discussed above, in another embodiment, hub 22 and wing assembly 26 may be integrally molded in a two-step molding process. In one embodiment, hub 22 may be formed from a thermoplastic material and wing assembly 26 may be formed of a flexible material.

In some embodiments, hub 22 and wing assembly 26 are separate pieces rather than being integrally molded. In one such embodiment, hub 22 and wing assembly 26 may be separate parts which are fixedly attached and secured through an appropriate medical grade adhesive, for example, epoxy or similar adhesive material. In other embodiments, hub 22 may be secured to wing assembly 26 by a snap fit mechanism, a locking tab mechanism, a spring loaded locking mechanism, a latch, or other similar mechanism.

Wing assembly 26 includes a body portion 64 extending between a pair of wings 66 and 68, i.e., a first wing 66 and a second wing 68. In an embodiment in which hub 22 and wing assembly 26 are separate parts, body portion 64 of wing assembly 26 may be fixedly attached to the underside 63 of hub 22, thereby allowing wings 66 and 68 to extend laterally from hub structure 46 at opposing sides thereof. Wing assembly 26 provides a component for assisting in positioning, stabilizing, and placement of shieldable needle device 12 and blood collection assembly 10 during a blood collection procedure. Wings 66 and 68 are preferably formed of a flexible material, and are movable between a relaxed, laterally extending position (FIGS. 6-8) in which they are substantially planar, to a bent dorsal position (FIGS. 2-5). In one embodiment, wings 66 and 68 may be a preformed bent structure. In other embodiments, wings 66 and 68 may also be a planar structure, for example, body portion 64 of wing assembly 26 may include skive portions 70 to assist in the folding of wings 66 and 68 from the laterally extending position to the dorsal position.

Referring to FIG. 1, shieldable needle device 12 includes tip guard assembly 24. Tip guard assembly 24 extends co-axially about needle cannula 20 and is axially movable along needle cannula 20 between a proximal position (FIGS. 2-5) adjacent hub 22 and a distal position (FIGS. 6-8) adjacent puncture tip 38 of needle cannula 20, as will be described in more detail later. With tip guard assembly 24 in the distal position, tip guard 24 protectively surrounds distal end 34 of needle cannula 20.

Figure 8:
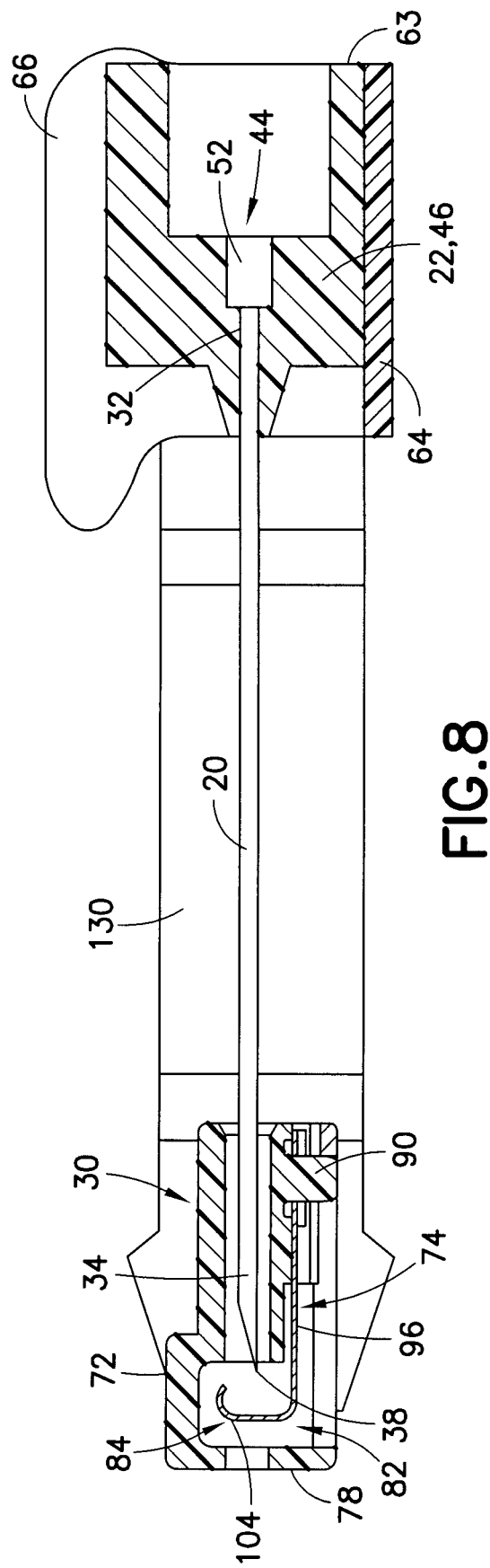
FIG. 8 is a cross-sectional view taken along line 8-8 of the shieldable needle device of FIG. 6 in accordance with an embodiment of the present invention.

Tip guard assembly 24 includes a tip guard housing 72 and a protective clip 74. Housing 72 is a unitary structure, desirably molded from a thermoplastic material, including a proximal end 76, a distal end 78, a recessed slot area 80 located at proximal end 76, and an internal chamber 82 (FIGS. 5 and 8) extending between the ends. A portion of internal chamber 82 adjacent distal end 78 defines an enlarged clip cavity 84, as shown in FIGS. 5 and 8. Additionally, tip guard assembly 24 includes structure for mating with first drive member 28 and second drive member 30. For example, a first side surface 92 of distal end 78 of tip guard housing 72 may include a connection element 86 for connection with first drive member 28. An opposing second side surface 94 of distal end 78 of tip guard housing 72 may also include a connection element 86 for connection with second drive member 30. In one embodiment, a first connection element 86 on first side surface 92 and a second connection element 86 on second side surface 94 may each include a button element 88 for connection with first drive member 28 and second drive member 30, respectively. In other embodiments, tip guard housing 72 may include different types of structures for mating with first drive member 28 and second drive member 30 as will be described in more detail below and with reference to FIGS. 9A-11. Tip guard housing 72 also includes a clip mounting post 90 (FIGS. 5 and 8) that extends downwardly from tip guard housing 72 at a location near proximal end 76 of tip guard housing 72.

Protective clip 74 is unitarily stamped and formed from a resiliently deflectable metallic material. Clip 74 includes a planar spring leg 96 with a proximal end 98 and an opposed distal end 100. A mounting aperture 102 extends through spring leg 96 at a location adjacent proximal end 98. Mounting aperture 102 has a diameter approximately equal to or slightly less than the diameter of clip mounting post 90 of tip guard housing 72. In this manner, clip mounting post 90 can be forced through mounting aperture 102 when the axis of clip mounting post 90 and the axis of mounting aperture 102 are substantially collinear. Clip 74 also includes a lock out leg 104 that extends from distal end 100 of spring leg 96. The extending lock out leg 104 enables secure protective engagement with puncture tip 38 of needle cannula 20 with tip guard assembly 24 in the distal position (FIGS. 6-8). The extending lock out leg 104 further enables smooth axial sliding movement of tip guard assembly 24 along needle cannula 20, as will be explained further below.

Hub 22 and tip guard assembly 24 are interconnected through first drive member 28 and second drive member 30. First drive member 28 and second drive member 30 provide for axial movement of tip guard assembly 24 along needle cannula 20 from a proximal position (FIGS. 2-5) adjacent hub 22 to a distal position (FIGS. 6-8) adjacent puncture tip 38 of needle cannula 20, as will be described in more detail later.

Referring to FIG. 1, shieldable needle device 12 includes first drive member 28 and second drive member 30. As discussed above, first drive member 28 is separate and distinct from second drive member 30. First drive member 28 includes a body 110 having a proximal end 112 and an opposing distal end 114. Similarly, second drive member 30 includes a body 130 having a proximal end 132 and an opposing distal end 134. Bodies 110 and 130 are desirably formed of a resilient flexible material capable of bending and/or extending without an application of force, such as silicone. For example, prior to use, the drive members 28 and 30 are in a folded biased position (FIGS. 2-5), and upon release of the wings 66 and 68, as will be described below, the drive members 28 and 30 extend forward to an extended position (FIGS. 6-8). In this manner, first drive member 28 and second drive member 30 move tip guard assembly 24 from the proximal position (FIGS. 2-5) to the distal position (FIGS. 6-8).

Proximal end 112 of body 110 of first drive member 28 includes structure for mating with hub 22. For example, in one embodiment, proximal end 112 may include two proximal openings 116 for receiving the connection elements 48 and 50 on first side surface 58 of distal end 42 of hub 22, thereby securing the proximal end 112 of first drive member 28 to the distal end 42 of hub 22. Distal end 114 of body 110 of first drive member 28 includes structure for mating with tip guard housing 72. For example, in one embodiment, distal end 114 of body 110 of first drive member 28 may include a distal opening 118 to mate with first connection element 86 on first side surface 92 of tip guard assembly 24.

Similarly, proximal end 132 of body 130 of second drive member 30 includes structure for mating with hub 22. For example, in one embodiment, proximal end 132 may include two proximal openings 136 for receiving the connection elements 48 and 50 on second side surface 60 of distal end 42 of hub 22, thereby securing the proximal end 132 of second drive member 30 to the distal end 42 of hub 22. Distal end 134 of body 130 of second drive member 30 includes structure for mating with tip guard housing 72. For example, in one embodiment, distal end 134 of body 130 of second drive member 30 may include a distal opening 138 to mate with second connection element 86 on second side surface 94 of tip guard assembly 24.

Alternatively or in addition to the mechanical mating structure described above for the connection of drive members 28 and 30 to hub 22 and tip guard assembly 24, respectively, the drive members 28 and 30 may be connected to hub 22 and tip guard assembly 24 through the use of an adhesive or similar connection mechanism.

Since drive members 28 and 30 are connected to hub 22, and since the wings 66 and 68 extend laterally from hub 22, movement of the wings 66 and 68 results in the corresponding movement of drive members 28 and 30. For example, with the wings 66 and 68 in the dorsal position (FIGS. 2-5), the wings 66 and 68 retain the first drive member 28 and the second drive member 30 in the folded biased position thereby maintaining tip guard assembly 24 in the proximal position. Additionally, with the wings 66 and 68 in the dorsal position, a gap 150 (FIG. 4) is formed between hub 22 and the wings 66 and 68 thereby retaining a portion of the first drive member 28 and a portion of the second drive member 30 internally within gap 150. In this manner, tip guard assembly 24 is maintained in a proximal position adjacent hub 22. Upon release of wings 66 and 68, wings 66 and 68 are free to move automatically from the dorsal position (FIGS. 2-5), in which the wings 66 and 68 are bent together to form a unitary dorsal structure, to the relaxed, laterally extending position (FIGS. 6-8). In this manner, first drive member 28 and second drive member 30 are no longer retained by wings 66 and 68 within gap 150, and first drive member 28 and second drive member 30 are able to unfold to the extended position (FIGS. 6-8) to move tip guard assembly 24 from the proximal position to the distal position. In other words, since first drive member 28 and second drive member 30 are fixedly attached to tip guard assembly 24, and since tip guard assembly 24 is axially movable along needle cannula 20, the release of wings 66 and 68 causes first drive member 28 and second drive member 30 to unfold and axially move tip guard assembly 24 in a direction generally along arrow B (FIG. 6) away from hub 22 and toward distal end 32 of needle cannula 20, where tip guard assembly 24 can effectively shield and protectively surround puncture tip 38 of needle cannula 20.

Body 110 of first drive member 28 and body 130 of second drive member 30 are formed of flexible materials that are biased toward the extended position, and therefore act as a means for storing energy to extend first drive member 28 and second drive member 30 toward distal end 34 of needle cannula 20 upon corresponding movement between wings 66 and 68 as described above, thereby propelling tip guard assembly 24 from the proximal position (FIGS. 2-5) to the distal position (FIGS. 6-8).

As discussed above, different types of structures can be used to connect first drive member 28 or second drive member 30 to hub 22 or tip guard assembly 24. FIGS. 9A-11 illustrate exemplary embodiments of different types of connection structures.

Referring to FIGS. 9A and 9B, a connection structure 200 includes a drive member receiving portion 202 and a locking portion 204 hingedly connected via a hinge 206. Drive member receiving portion 202 includes a receiving surface 208 and a post 210 extending from receiving surface 208. Locking portion 204 defines an aperture 216 and includes latch members 212 having locking ends 214.

Referring to FIGS. 9A and 9B, a drive member 28A includes a body 110A having a proximal end 112A defining an opening 116A. To secure drive member 28A to connection structure 200, opening 116A of body 110A is disposed over post 210 of drive member receiving portion 202 as shown in FIG. 9A. In this position, locking portion 204 can be pivoted in a direction generally along arrow C (FIG. 9A) about hinge 206 to the locking position shown in FIG. 9B. In this locking position, post 210 of drive member receiving portion 202 is received within aperture 216 of locking portion 204 and locking ends 214 of latch members 212 are lockingly engaged with drive member receiving portion 202 to provide a secure connection between drive member 28A and connection structure 200. Connection structure 200 can be used with hub 22 or tip guard assembly 24 to securely connect first drive member 28 or second drive member 30 to hub 22 or tip guard assembly 24.

Figure 10:
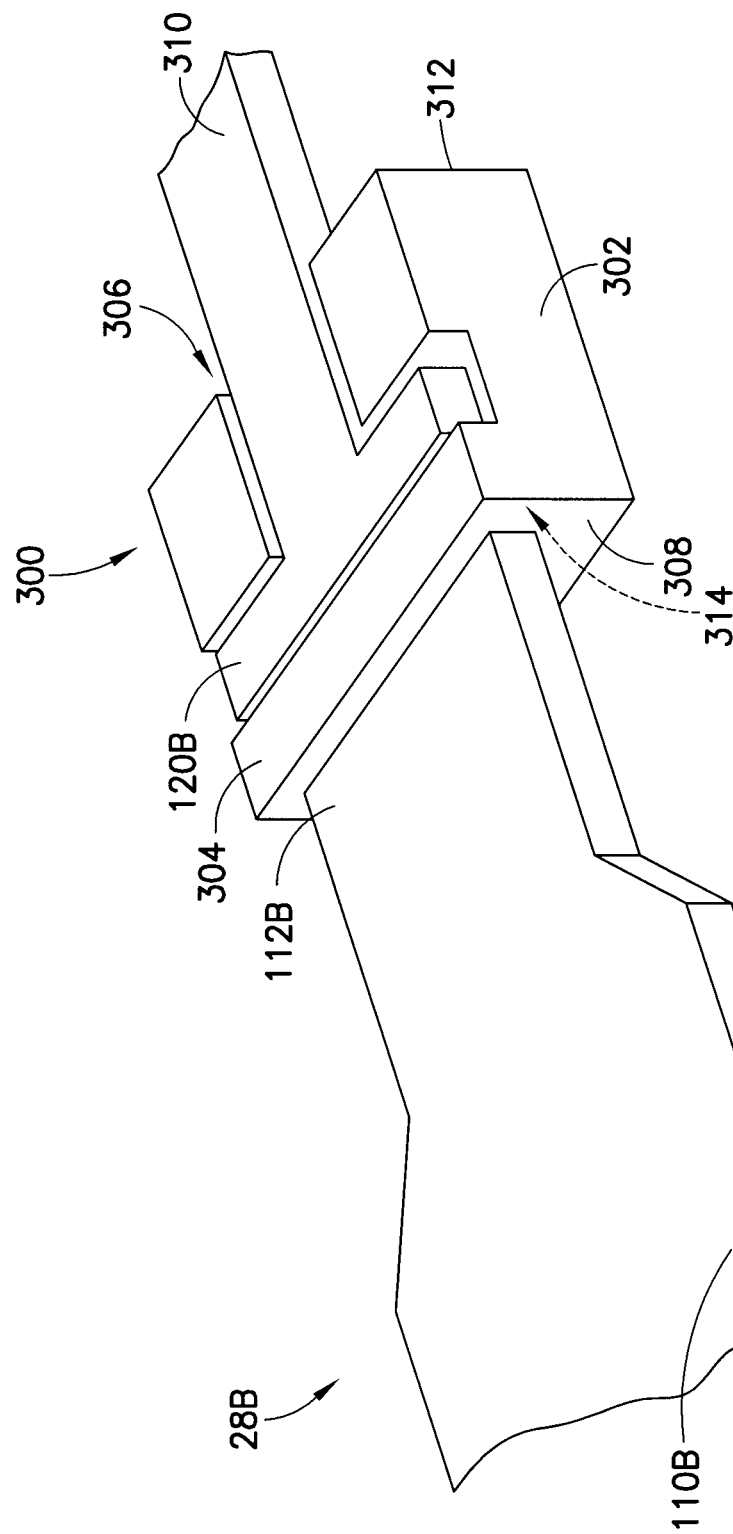
FIG. 10 is a perspective view of another exemplary connection means, in a locked position, between a first drive member or a second drive member and a hub or a tip guard assembly of the shieldable needle device of FIG. 1 in accordance with an embodiment of the present invention.

Referring to FIG. 10, a connection structure 300 includes a drive member receiving portion 302 having a locking wall 304 at a distal end 308 and defining a receiving channel 306 at a proximal end 312. Drive member receiving portion 302 also defines a drive member receiving slot 314 at distal end 308. Referring to FIG. 10, a drive member 28B includes body a 110B having a proximal end 112B and a protruding portion 120B located adjacent proximal end 112B. Protruding portion 120B may be formed of a deformable resilient material.

To secure drive member 28B to connection structure 300, protruding portion 120B of body 110B of drive member 28B is inserted into receiving slot 314 of connection structure 300 so that protruding portion 120B can slide through and past locking wall 304. Because protruding portion 120B is formed of a deformable resilient material, locking wall 304 can deform protruding portion 120B as protruding portion 120B slides through receiving slot 314. Once protruding portion 120B extends beyond locking wall 304, protruding portion 120B is able to return back to its original form as shown in FIG. 10. Once protruding portion 120B is in the locked position of FIG. 10, locking wall 304 forms a physical barrier that locks protruding portion 120B within slot 314 so that drive member 28B can not be pulled out of connection structure 300. Connection structure 300 can be used with hub 22 or tip guard assembly 24 to securely connect first drive member 28 or second drive member 30 to hub 22 or tip guard assembly 24. For example, referring to FIG. 10, receiving channel 306 of connection structure 300 is capable of securely receiving a hub or a tip guard assembly 310.

Figure 11:
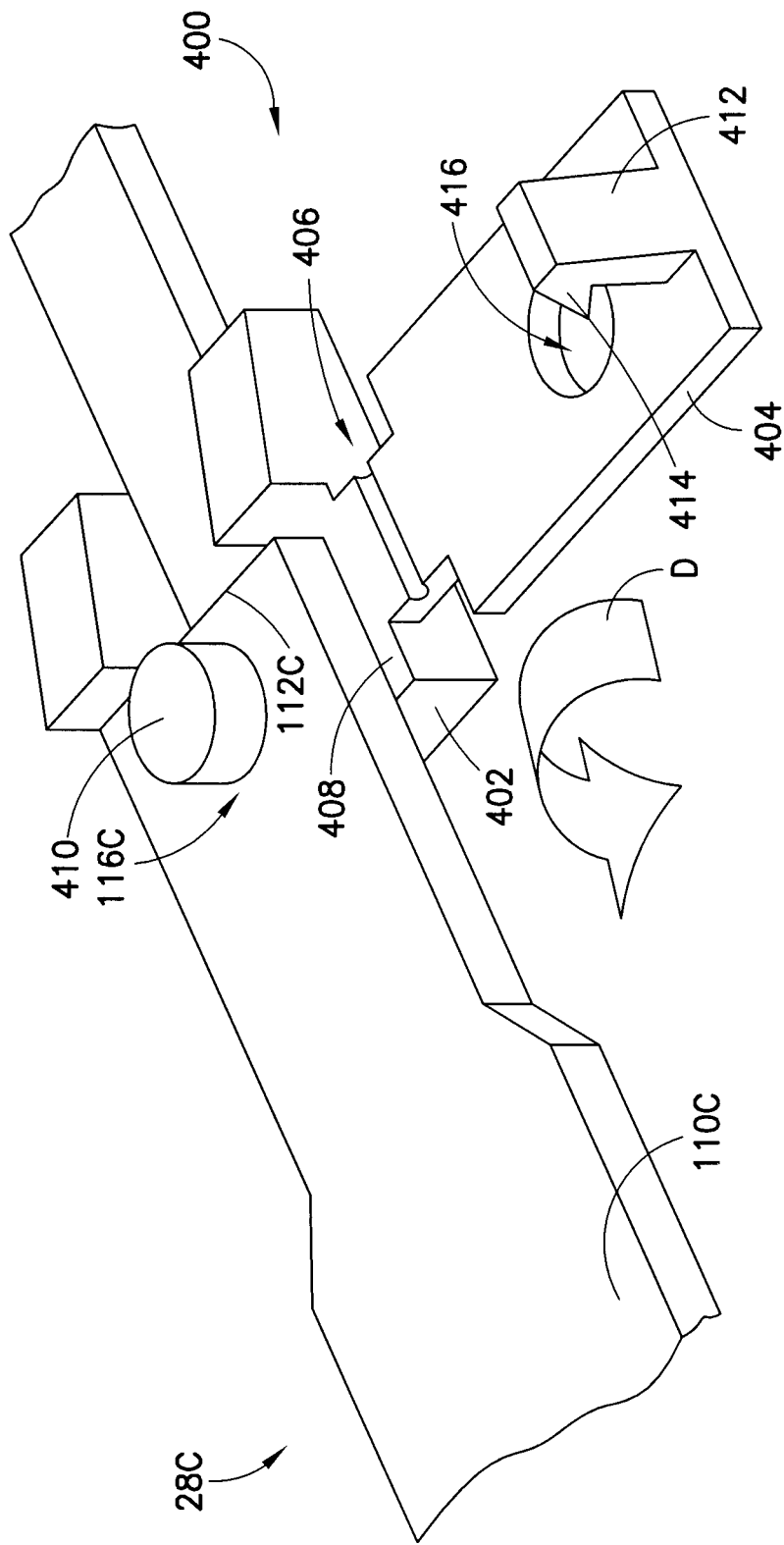
FIG. 11 is a perspective view of yet another exemplary connection means, in an open position, between a first drive member or a second drive member and a hub or a tip guard assembly of the shieldable needle device of FIG. 1 in accordance with an embodiment of the present invention.

Referring to FIG. 11, a connection structure 400 includes a drive member receiving portion 402 and a locking portion 404 hingedly connected via a hinge 406. Drive member receiving portion 402 includes a receiving surface 408 and a post 410 extending from receiving surface 408. Locking portion 404 defines an aperture 416 and includes a latch member 412 having a locking end 414.

Referring to FIG. 11, a drive member 28C includes a body 110C having a proximal end 112C defining an opening 116C. To secure drive member 28C to connection structure 400, opening 116C of body 110C is disposed over post 410 of drive member receiving portion 402 as shown in FIG. 11. In this position, locking portion 404 can be pivoted in a direction generally along arrow D (FIG. 11) about hinge 406 to a locking position. In the locking position, post 410 of drive member receiving portion 402 is received within aperture 416 of locking portion 404 and locking end 414 of latch member 412 is lockingly engaged with drive member receiving portion 402 to provide a secure connection between drive member 28C and connection structure 400. Connection structure 400 functions similarly to connection structure 200 described above. Connection structure 400 can be used with hub 22 or tip guard assembly 24 to securely connect first drive member 28 or second drive member 30 to hub 22 or tip guard assembly 24.

Figure 3:
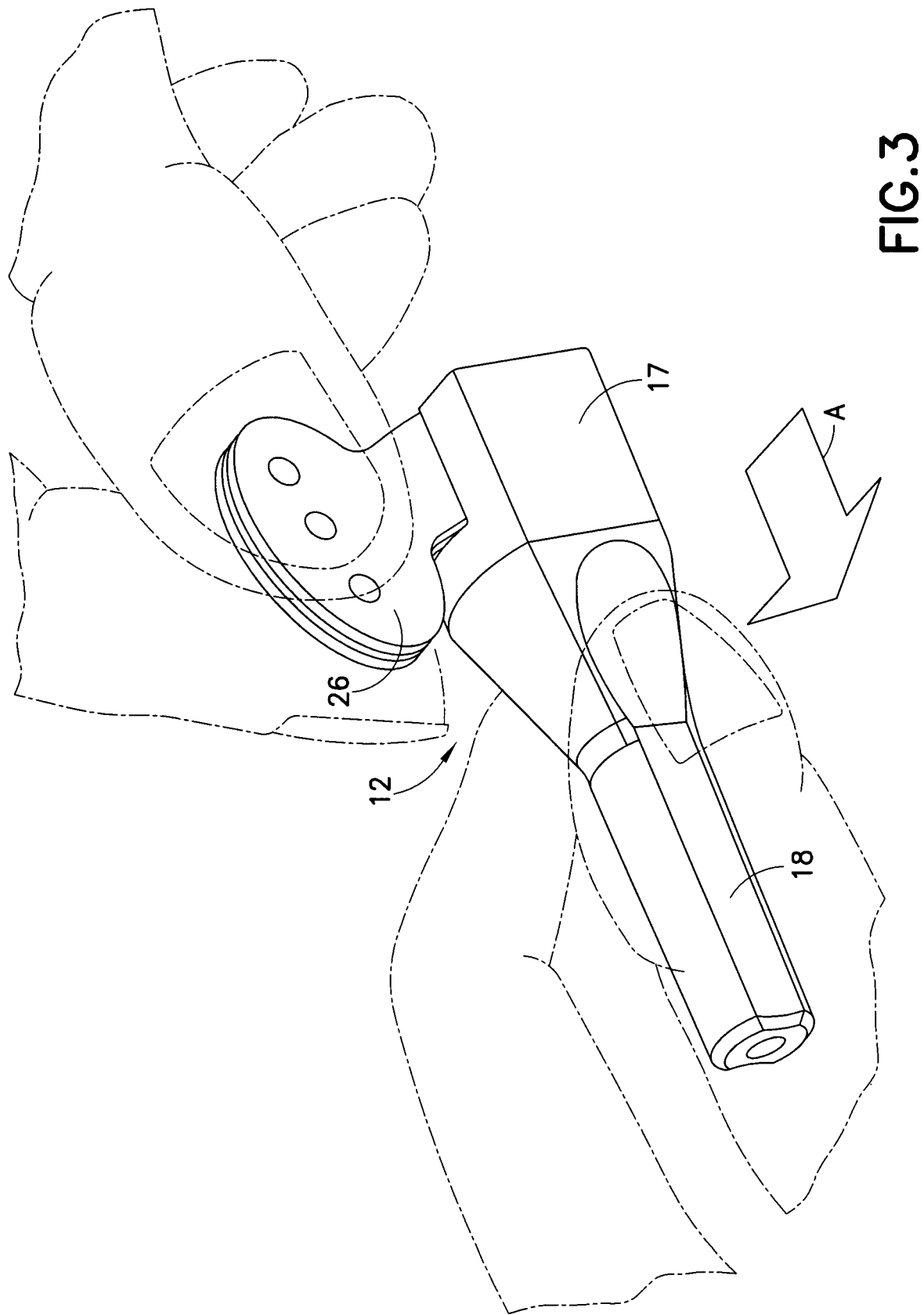
FIG. 3 is a perspective view of the shieldable needle device of FIG. 2 with a packaging cover being removed in accordance with an embodiment of the present invention.

Assembly of shieldable needle device 12 may be accomplished as follows. Tip guard assembly 24 is assembled by forcing clip mounting post 90 of tip guard housing 72 through mounting aperture 102 of protective clip 74. Spring leg 96 of clip 74 is then urged downwardly or away from internal chamber 82 through tip guard housing 72. First drive member 28 and second drive member 30 are then interconnected between tip guard assembly 24 and hub 22 by depressing proximal openings 116 and 136 over connection elements 48 and 50 on respective side surfaces 58 and 60 of hub 22 and depressing distal openings 118 and 138 over connection element 86 on respective side surfaces 92 and 94 of tip guard assembly, respectively, as described above. Distal end 34 of needle cannula 20 is then passed through central passage 44 of hub 22, and urged into internal chamber 82 at proximal end 76 of tip guard housing 72. The downward deflection of spring leg 96 enables distal end 34 of needle cannula 20 to be passed entirely through tip guard housing 72 as shown in FIG. 5. Spring leg 96 can be released after puncture tip 38 of needle cannula 20 passes entirely through tip guard housing 72. In this manner, the end of lock out leg 104 will be biased against and slide along needle cannula 20. Tip guard assembly 24 is then slid proximally along needle cannula 20 into a position adjacent hub 22, with first drive member 28 and second drive member 30 each folded over itself into a bent, biased position, primed for use, as shown in FIGS. 2-5. Wings 66 and 68 are then bent toward each other in the dorsal position to form a dorsally mating structure as shown in FIGS. 2-5. Packaging cover 18 is then urged over puncture tip 38 and urged proximally over needle cannula 20, with puncture tip 38 safely maintained and disposed within packaging cover 18, and with a lateral wall 17 and a slot 19 of packaging cover 18 maintaining wings 66 and 68 in the bent dorsal position as shown in FIGS. 2 and 3. Packaging cover 18 is desirably constructed of a rigid material which is capable of maintaining wings 66 and 68 in the dorsal position.

As discussed above, blood collection assembly 10 can be packaged substantially in the condition shown in FIG. 2 in protective packaging, such as in a blister package. Prior to use, blood collection assembly 10 is removed from any protective package, and fixture 16 may be connected to an appropriate receptacle for providing fluid communication with lumen 36 extending through needle cannula 20.

In use, blood collection assembly 10 is provided with shieldable needle device 12 assembled and including flexible tube 14 extending from shieldable needle device 12 and connected to fixture 16. After removing blood collection assembly 10 from its protective packaging, it can be assembled with other appropriate medical equipment for use. For example, a non-patient needle assembly and a needle holder may be connected to blood collection assembly 10 through fixture 16.

To prepare for use of blood collection assembly 10, the user grasps blood collection assembly 10 at shieldable needle device 12, placing a thumb and forefinger on wings 66 and 68, with wings 66 and 68 maintained in a dorsal position between the user's fingers, as shown in FIG. 3. Both wings 66 and 68 are preferably flexed or bent toward each other between a user's thumb and forefinger with bodies 110 and 130 of first and second drive members 28 and 30 trapped therebetween. Packaging cover 18 is then grasped and urged distally in a direction generally along arrow A (FIG. 3) to disengage cover 18 from needle cannula 20, thereby exposing puncture tip 38 of needle cannula 20.

The medical practitioner can then urge puncture tip 38 at distal end 34 of needle cannula 20 into a targeted blood vessel of a patient, while wings 66 and 68 are maintained between thumb and forefinger to assist in a controlled entry by the medical practitioner. Tip guard assembly 24 is maintained in the proximal position (FIGS. 3-5) due to the grip by the user's fingers between wings 66 and 68, which maintains first drive member 28 and second drive member 30 in the folded, biased position.

After the targeted blood vessel has been accessed, the medical practitioner can release wings 66 and 68. Once the user releases the device, first drive member 28 and second drive member 30 are free to move from the folded biased position to the extended unfolded position, due to the bias exerted by bodies 110 and 130 of first drive member 28 and second drive member 30 through release of wings 66 and 68. Such movement causes bodies 110 and 130 of first drive member 28 and second drive member 30 to extend, thereby propelling tip guard assembly 24 distally along needle cannula 20 in an axial direction generally along arrow B (FIG. 6), with tip guard assembly 24 sliding or gliding along needle cannula 20 toward distal end 34. Distal movement of tip guard assembly 24 will terminate when distal end 78 of tip guard housing 72 contacts the skin of the patient near the puncture site.

Upon completion of the procedure, such as when all desired samples have been drawn, needle cannula 20 is withdrawn from the patient. This removal of needle cannula 20 from the patient will permit further extension of bodies 110 and 130 of first drive member 28 and second drive member 30 and a corresponding distal movement of tip guard assembly 24 in an axial direction generally along arrow B (FIG. 6). After tip guard assembly 24 is moved along needle cannula 20 to the distal end 34, lock out leg 104 of clip 74 will pass distally beyond puncture tip 38 of needle cannula 20. The inherent resiliency of spring leg 96 of clip 74 will urge lock out leg 104 over puncture tip 38 of needle cannula 20 as shown in FIG. 8. In this manner, a return movement of tip guard assembly 24 to the proximal position is prevented. Furthermore, first drive member 28 and second drive member 30 have overall dimensions that will prevent movement of tip guard assembly 24 distally beyond needle cannula 20. In this manner, puncture tip 38 of needle cannula 20 is safely shielded. Blood collection assembly 10 may then be appropriately and safely discarded.

Figure 4:
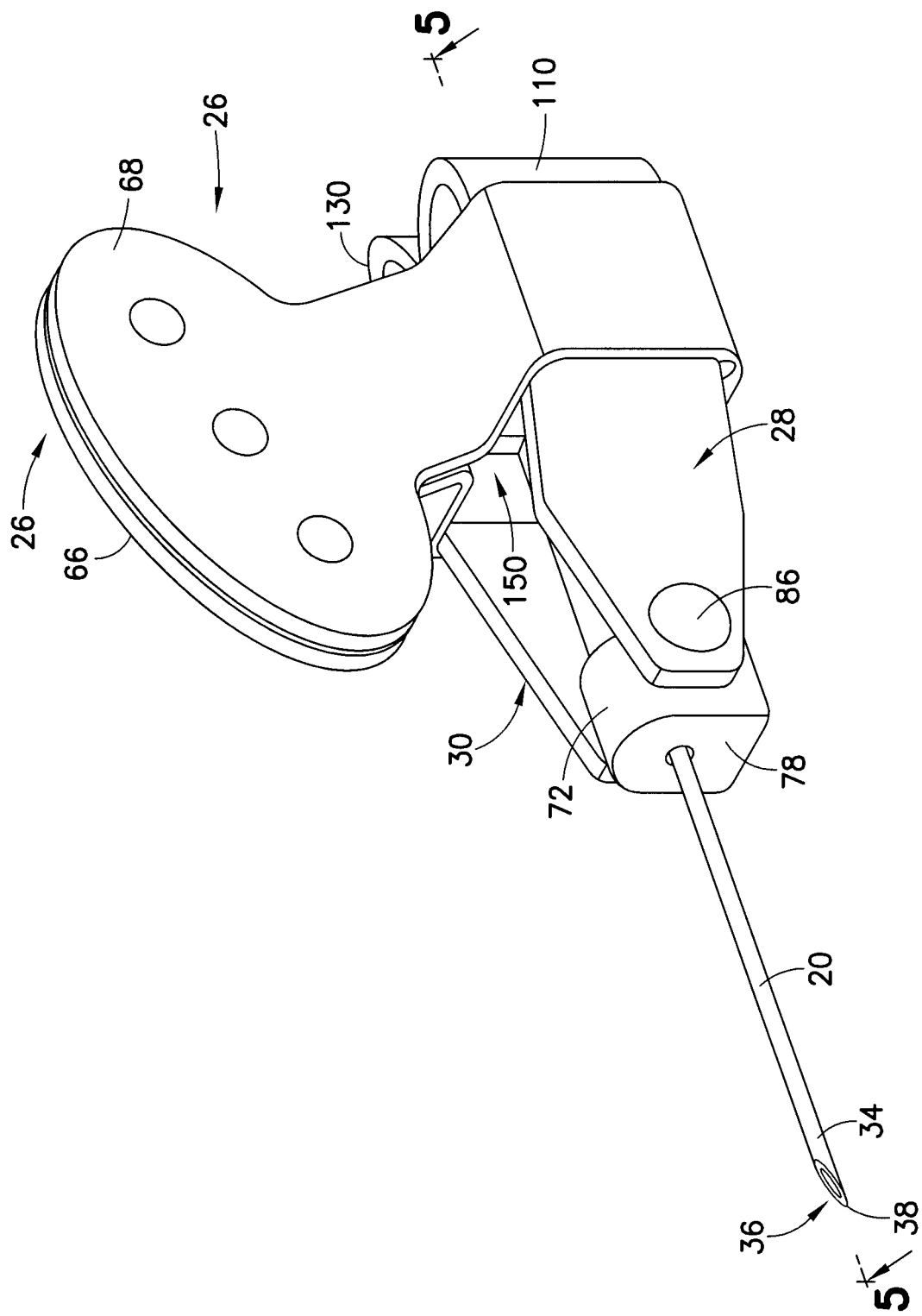
FIG. 4 is a perspective view of the shieldable needle device of FIG. 2 with the packaging cover removed, with a wing assembly in a dorsal position, and first and second drive members in a folded biased position in accordance with an embodiment of the present invention.

Since wings 66 and 68 are initially bent in a dorsal position, wings 66 and 68 can act as a handle portion during insertion, withdrawal, and disposal of shieldable needle device 12. In particular, after release of wings 66 and 68 to propel tip guard assembly 24 to the distal position, the needle cannula 20 is shielded and wings 66 and 68 extend laterally from hub 22. Since wings 66 and 68 include at least some flexible portion, wings 66 and 68 can be bent to a dorsal position, as shown in FIG. 4, to allow a user to grip the shieldable needle device 12 for removal from the patient. The wings 66 and 68 can also act as a handle portion for carrying blood collection assembly 10 at a position remote from the used needle tip of cannula 20. Additionally, first drive member 28 and second drive member 30 can be actuated while puncture tip 38 is within the patient's blood vessel, thereby beginning axial movement of tip guard assembly 24 along needle cannula 20. In other embodiments, first drive member 28 and second drive member 30 can be actuated after puncture tip 38 is removed from the patient's blood vessel.

The shielding feature of the present invention is passively activated upon normal usage of the device. In particular, upon removal of the packaging cover prior to insertion, the safety feature is primed and charged, ready for shielding the needle once the user releases the wing structure after insertion into a patient. Moreover, as described above, passive shielding of the needle cannula is automatically achieved merely by removing the needle cannula from the patient.

In some instances, the needle device may be dropped or knocked from the hand of the medical practitioner either before venipuncture or during a medical procedure. The passive shielding described above will commence automatically when the needle device is dropped or knocked from the medical practitioner's hand. Thus, the automatic shielding may be triggered by the intentional or unintentional release of the wings by the medical practitioner.

Moreover, a medical practitioner does not always enter the targeted blood vessel during the first venipuncture attempt. However, a medical practitioner typically retains a close grip on the needle device until the targeted blood vessel has been entered. In this manner, the continued gripping of the wings will prevent the needle from shielding until the targeted blood vessel has been punctured. The second attempt at accessing a targeted blood vessel generally is a very low risk procedure in which the practitioner's hand is spaced considerably from the puncture tip of the needle cannula. Thus, the blood collection set according to the present invention does not involve the inconvenience of having to use a new blood collection set following each unsuccessful venipuncture attempt.

While the needle assembly of the present invention has been described in terms of one embodiment for use in connection with a blood collection system, it is further contemplated that the needle assembly could be used with other medical procedures, such as in conjunction with a conventional intravenous infusion set, which are well known in the art for use with needle assemblies.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A shieldable needle device comprising: a needle cannula having a proximal end and a distal end; a hub supporting at least a portion of the needle cannula; a tip guard axially movable with respect to the needle cannula from a first position adjacent the hub to a second position in which the tip guard shields the distal end of the needle cannula; a first drive member extendable between a biased position and an extended position for moving the tip guard from the first position to the second position, the first drive member having a proximal end engaged with the hub and a distal end engaged with the tip guard; a second drive member separate and distinct from the first drive member, the second drive member extendable between a biased position and an extended position for moving the tip guard from the first position to the second position, the second drive member having a proximal end engaged with the hub and a distal end engaged with the tip guard; and a pair of wings extending from opposing lateral sides of the hub, the pair of wings separate from the first drive member and the second drive member, the pair of wings movable between a dorsal position in which the wings are bent together toward each other to form a structure that retains the first drive member and the second drive member in the biased position thereby maintaining the tip guard in the first position and a laterally extending position in which the wings extend laterally from the opposing lateral sides of the hub, wherein with the wings in the dorsal position, the first drive member is retained between a first hub lateral side and a first wing lateral side and the second drive member is retained between a second hub lateral side and a second wing lateral side, wherein, with the pair of wings in the dorsal position, the pair of wings retain the first drive member and the second drive member in the biased position thereby maintaining the tip guard in the first position, and movement of the pair of wings from the dorsal position to the laterally extending position releases the first drive member and the second drive member thereby allowing the first drive member and the second drive member to transition to the extended position and advance the tip guard from the first position to the second position; wherein, when the first drive member and the second drive member are each in the extended position, the first drive member and the second drive member contact each other along a length of the needle cannula between the hub and the tip guard such that the first drive member, the second drive member, and the tip guard encapsulates the needle cannula along the length of the needle cannula.

2. The shieldable needle device of claim 1, wherein the proximal end of the first drive member is connected to an opposite side of the hub from the proximal end of the second drive member.

3. The shieldable needle device of claim 1, wherein the distal end of the first drive member is connected to an opposite side of the tip guard from the distal end of the second drive member.

4. The shieldable needle device of claim 1, further comprising a cover protectively surrounding the needle cannula and maintaining the pair of wings in the dorsal position.

5. The shieldable needle device of claim 4, wherein the cover defines a slot area for receiving and maintaining the pair of wings in the dorsal position.

6. The shieldable needle device of claim 1, wherein the pair of wings are formed with the hub.

7. The shieldable needle device of claim 1, wherein the pair of wings are formed of a resilient flexible material.

8. The shieldable needle device of claim 1, wherein the first drive member and the second drive member are formed of a resilient flexible material.

9. The shieldable needle device of claim 1, wherein the tip guard comprises a tip guard housing formed from a plastic material and a metallic spring clip mounted to the tip guard housing, the spring clip biased against the needle cannula with the tip guard in the first position and the spring clip disposed over the distal end of the needle cannula with the tip guard in the second position.

10. The shieldable needle device of claim 1, wherein both the first drive member and the second drive member are at least partially folded in the biased position.

11. The shieldable needle device of claim 1, further comprising:
the hub having a first side surface including a first connection element and a second side surface including a second connection element;
the first drive member having a first drive member connection element; and
the second drive member having a second drive member connection element, wherein the first drive member connection element is connected with the first connection element and the second drive member connection element is connected with the second connection element.

* * * * *